(12) United States Patent
Tarasova et al.

(10) Patent No.: US 8,008,316 B2
(45) Date of Patent: Aug. 30, 2011

(54) AZONAFIDE DERIVED TUMOR AND CANCER TARGETING COMPOUNDS

(75) Inventors: Nadya I. Tarasova, Frederick, MD (US); Marcin Dyba, Frederick, MD (US); Christopher J. Michejda, North Potomac, MD (US); Maria Michejda, legal representative, North Potomac, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 276 days.

(21) Appl. No.: 12/441,029

(22) PCT Filed: Sep. 12, 2007

(86) PCT No.: PCT/US2007/078233
§ 371 (c)(1),
(2), (4) Date: May 1, 2009

(87) PCT Pub. No.: WO2008/033891
PCT Pub. Date: Mar. 20, 2008

(65) Prior Publication Data
US 2010/0120817 A1    May 13, 2010

Related U.S. Application Data

(60) Provisional application No. 60/844,027, filed on Sep. 12, 2006.

(51) Int. Cl.
*A61K 31/473* (2006.01)
*C07D 221/18* (2006.01)

(52) U.S. Cl. ............ 514/284; 546/76; 544/361; 514/2; 514/253

(58) Field of Classification Search ............ 514/284, 514/253, 2; 546/76; 544/361
See application file for complete search history.

(56) References Cited

U.S. PATENT DOCUMENTS
5,635,506 A    6/1997    Alberts et al.
5,703,089 A    12/1997   Braña et al.

FOREIGN PATENT DOCUMENTS
WO    WO 92/00281 A1      1/1992
WO    WO 03/072754 A3     9/2003
WO    WO 2006/060533 A3   6/2006

OTHER PUBLICATIONS

Czerwinski et al., "Cytotoxic agents directed to peptide hormone receptors: Defining the requirements for a successful drug," *PNAS*, 95, 11520-11525 (1998).

Dorr et al., "Preclinical antitumor activity of the azonafide series of anthracene-based DNA intercalators," *Anticancer Drugs*, 12 (3), 213-220 (2001).
Dyba et al., "Small Molecule Toxins Targeting Tumor Receptors," *Curr. Pharm. Des.*, 10, 2311-2334 (2004).
Jaracz et al, "Recent advances in tumor-targeting anticancer drug conjugates," *Bioorg. Med. Chem.*, 13, 5043-54 (2005).
Langer, "New Methods of Drug Delivery," *Science*, 249, 1527-1533 (1990).
Sami et al., "2-substituted 1,2-Dihydro-3H-dibenz[de,h]isoquinoline-1,3-diones. A new class of antitumor agent," *J. Med. Chem.*, 36, 765-770 (1993).
Sami et al., "Amino-Substituted 2-[2'-(dimethylamino)ethyl]-1,2-dihydro-3H-dibenz[de,h]isoquinoline-1,3-diones. Synthesis, antitumor activity, and quantitative structure—activity relationship," *J. Med. Chem.*, 38, 983-993 (1995).
Sami et al., "6- and 7-substituted 2-[2'-(Dimethylamino)ethyl]-1,2-dihydro-3H-dibenz[de,h] isoquinoline-1,3-diones: synthesis, nucleophilic displacements, antitumor activity, and quantitative structure-activity relationships," *J. Med. Chem.*, 39, 1609-1618 (1996).
Sami et al., "2-[2'-(Dimethylamino)ethyl]-1,2-dihydro-3H-dibenz[de,h]isoquinoline-1,3-diones with substituents at positions 4, 8, 9, 10, and 11. Synthesis, antitumor activity, and quantitative structure-activity relationships," *J. Med. Chem.*, 39, 4978-87 (1996).
Sami et al., "Analogues of amonafide and azonafide with novel ring systems," *J. Med. Chem.*, 43, 3067-3073 (2000).

*Primary Examiner* — Charanjit Aulakh
(74) *Attorney, Agent, or Firm* — Leydig, Voit & Mayer, Ltd.

(57) ABSTRACT

An azonafide-based compound of Formula I, a composition comprising the compound, and a method of using the compound to deliver a cytotoxic azonafide derivative to a cell, as well as related compounds and methods for the use thereof to pre-pare an azonafide-based compound of Formula I.

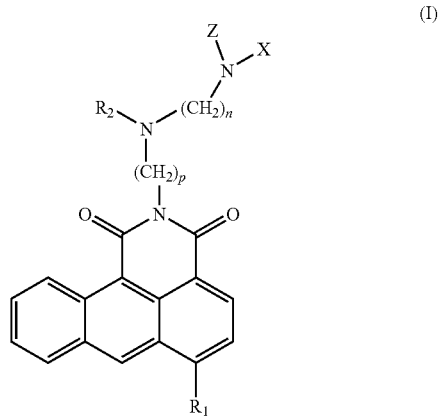

39 Claims, No Drawings

AZONAFIDE DERIVED TUMOR AND CANCER TARGETING COMPOUNDS

CROSS-REFERENCE TO RELATED APPLICATIONS

This patent application is a U.S. National Phase of International Patent Application No. PCT/US07/78233, filed Sep. 12, 2007, which claims the benefit of U.S. Provisional Patent Application No. 60/844,027, filed Sep. 12, 2007, which are incorporated in their entirety herein by this reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 6,952 Byte ASCII (Text) file named "704387ST25.TXT," created on Feb. 2, 2009.

BACKGROUND OF THE INVENTION

Systemic toxicity of drugs is one of the most serious problems of cancer chemotherapy and frequently is dose limiting. Such is true of the azonafides, which are a series of anthracene-based DNA intercalcators that inhibit tumor growth at low concentrations and are not typically affected by multidrug resistance phenomena. Don et al., *Anticancer Drugs*, 12(3), 213-20 (2001).

There exists a continuing need in the art for improved azonafide-based compounds with reduced toxicity. The present invention provides such compounds and methods for the use and preparation thereof. These and other objects of the invention, as well as additional inventive features, will be apparent from the description of the invention provided herein.

BRIEF SUMMARY OF THE INVENTION

The invention provides a compound of Formula I:

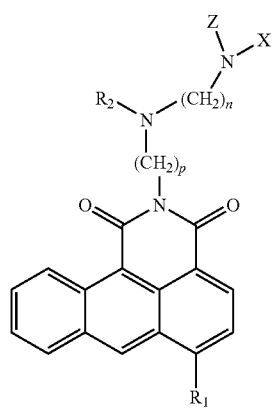

Formula I wherein n is 1-8;
p is 2-4;
X is —(CH$_2$)$_q$NH-A, —(CH$_2$)$_q$NH-A-B, —(CH$_2$)$_q$NH-A-W—B, -A, -A-B, -A-W—B, —W-A, —W-A-B, or —W-A-W—B, wherein A is a peptide comprising two or more amino acids, B is a cell-targeting construct, W is a coupling moiety selected from the group consisting of —(CH$_2$)$_m$NH—, —C(O)(CH$_2$)$_m$C(O)—, —C(O)(CH$_2$)$_m$—, or

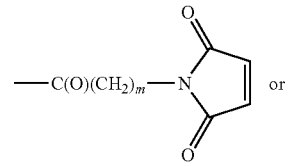

m is 1-16 and q is 1-8;
Z is hydrogen, methyl, or, when n is 2 and R$_2$ is —(CH$_2$)$_2$—, Z is a bond between R$_2$ and the nitrogen to which Z is attached;
R$_1$ is selected from the group consisting of hydrogen, alkyl, alkyoxy, alkynoyl, alkylthiol, formyl, halogen, aryl, nitro, sulfanyl, hydrazino, amino, oxyamino, alkylamino, dialkylamino, and combinations thereof; and
R$_2$ is selected from the group consisting of hydrogen, alkyl, alkyoxy, alkynoyl, alkylthiol, formyl, halogen, aryl, nitro, sulfanyl, hydrazino, amino, oxyamino, alkylamino, dialkylamino, and combinations thereof, or R$_2$ can be —(CH$_2$)$_2$—.

The invention also provides a compound of Formula II:

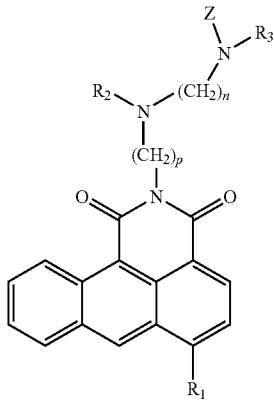

Formula II wherein n is 1-8;
p is 2-4;
R$_3$ is H, —(CH$_2$)$_q$NH$_2$, —(CH$_2$)$_q$NH—Y, —(CH$_2$)$_q$NH-A-Y, —Y, or -A-Y, wherein A is a peptide comprising two or more amino acids, Y is a coupling moiety selected from the group consisting of

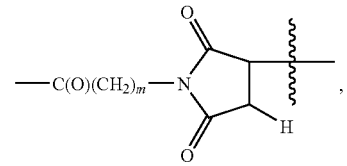

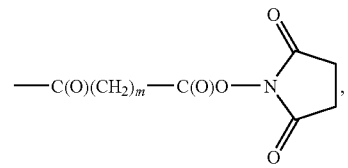

m is 1-16 and q is 1-8;

Z is hydrogen, methyl, or, when n is 2 and $R_2$ is —$(CH_2)_2$—, Z is a bond between $R_2$ and the nitrogen to which Z is attached;

$R_1$ is selected from the group consisting of hydrogen, alkyl, alkyoxy, alkynoyl, alkylthiol, formyl, halogen, aryl, nitro, sulfanyl, hydrazino, amino, oxyamino, alkylamino, dialkylamino, and combinations thereof; and $R_2$ is selected from the group consisting of hydrogen, alkyl, alkyoxy, alkynoyl, alkylthiol, formyl, halogen, aryl, nitro, sulfanyl, hydrazino, amino, oxyamino, alkylamino, dialkylamino, and combinations thereof, or $R_2$ can be —$(CH_2)_2$—.

The invention further provides a method of delivering a cytotoxic azonafide derivative to a cell comprising administering to the cell a compound of Formula I, whereupon a cytotoxic azonafide derivative is released from the compound and delivered to the cell.

The invention additionally provides a method for preparing a compound of Formula I comprising linking a peptide or peptidomimetic to the $R_3$ group of a compound of Formula II, whereby a compound of Formula I is prepared.

DETAILED DESCRIPTION OF THE INVENTION

The compound of Formula I, according to preferred embodiments, can be used to deliver a cytotoxic azonafide derivative to a cell while reducing the toxic side effects associated with systemic administration of azonafide compounds. Without wishing to be bound by any particular theory, it is believed that the compound of Formula I comprising a peptide at position X, optionally with a cell receptor-targeting ligand, has reduced toxicity as compared to the corresponding molecule without a peptide and optional ligand at position X. It is further believed that the compound of Formula I is stable when in the general circulation of a mammal, but the peptide is cleaved upon specific cellular interaction with the compound (e.g., interaction with cell-surface receptors) or upon interaction with proteases secreted by cancer cells or residing on the surface of cancer cells, thereby releasing a toxic moiety.

According to Formula I, n can be any integer from 1-8 (e.g., 1, 2, 3, 4, 5, 6, 7, or 8). Preferably, n is 1-6 (e.g., 2-5), or even 1-4 (e.g., 2-4) or 1-3 (e.g., 2 or 3). Likewise, p can be any integer from 2-4 (e.g., 2, 3, or 4).

X of Formula I can be —$(CH_2)_q$NH-A, —$(CH_2)_q$NH-A-B, —$(CH_2)_9$NH-A-W—B, -A, —A-B, -A-W—B, —W-A, —W-A-B, or —W-A-W—B, wherein A is a peptide comprising two or more amino acids, B is a ligand, and W is a coupling moiety selected from the group consisting of —$(CH_2)_m$NH—, —$C(O)(CH_2)_mC(O)$—; —$C(O)(CH_2)_m$—, or

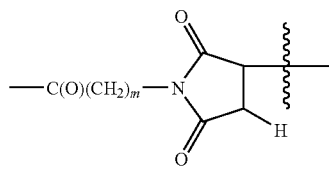

wherein m is an integer from 1-16 (e.g., 1, 2, 3, 4, 5, 6, 7, 8, 9, 10, 11, 12, 13, 14, 15, 16), and q is an integer from 1-8 (e.g., 1, 2, 3, 4, 5, 6, 7, or 8). Preferably, m is 1-12, 1-10, or 1-8. More preferably, m is at least 2 (e.g., 2-12, 2-10, 2-8, 2-6, or 2-4). Preferably, q is 1-6, or even 1-4 or 1-3 (e.g., 2 or 3). More preferably, q is at least 2 (e.g., 2-6 or 2-4).

Z can be hydrogen or a methyl group such as —$CH_3$, or when n is 2 and $R_2$ is —$(CH_2)_2$—, Z can be a bond between $R_2$ and the nitrogen to which Z is attached. Thus, it is within the scope of the present invention that $R_2$, Z, and $(CH_2)$ are optionally taken together with the nitrogen atoms to which they are attached to form a piperazine moiety.

A can be any suitable peptide. The term "peptide" as used herein refers generally to a polyamide that comprises two or more amino acids. Preferably, the peptide comprises no more than 10 amino acids (e.g., comprises 2-10 or 3-10 amino acids), such as no more than 8 amino acids (e.g., 2-8 or 3-8 amino acids) or no more than 5 or 6 amino acids (e.g., 2-5, 2-6, 3-5, or 3-6 amino acids). Alternatively, or additionally, the peptide (A) preferably comprises the amino acid sequence "ALA" or "LAL," wherein ALA and LAL are not mutually exclusive (e.g., ALAL comprises both). Specific examples of useful peptides are disclosed in U.S. Patent Application Publication No. 2005/0171014 A1, including VLALA (SEQ ID NO: 1), FALA (SEQ ID NO: 2), ALAL (SEQ ID NO: 3), ALALA (SEQ ID NO: 4), ChaLALA (SEQ ID NO: 5), ChaChaLAL (SEQ ID NO: 6), NalChaLAL (SEQ ID NO: 7), NalLALA (SEQ ID NO: 8), and combinations thereof, wherein "Cha" is an abbreviation for 2-cyclohexyl-L-alanine, and "Nal" is an abbreviation for 1-naphthyl-alanine. It is generally appreciated by one skilled in the art that a peptide linker can optionally be glycosylated, amidated, carboxylated, phosphorylated, esterified, N-acetylated, or converted into an acid addition salt and/or dimerized or polymerized.

B can be any suitable cell-targeting construct. The term "cell-targeting construct" as used herein refers to any construct that targets a particular cell type, such as a cancer cell. Cell-targeting constructs can target a cell, such as a cancer cell, by interacting with, or binding to, cell-surface receptors or other molecules on the cell surface. Cell targeting constructs also can target cells, such as cancer cells, by interacting with proteins secreted by the cell. For example, the cell-targeting construct can be a peptide or antibody that binds to a cell surface receptor of a cancer cell or the cell-targeting construct can be a peptide that is cleaved by a protease residing on the surface of a cancer cell, or a protease secreted by a cancer cell (and, thus, is concentrated in the locality of the cancer). Upon such interaction, a cytotoxic compound is released from the compound of Formula I. Compounds that target cancer cells by other mechanisms also can be used.

The cell-targeting construct should comprise a functional group that can attach to (e.g., form a bond with) the carboxy-terminus or, preferably, the amino-terminus of peptide A, or to a suitable coupling agent, such as a coupling agent comprising a maleimido or succinimide functional group. Typically, the peptide (A) is attached to the azonafide ring structure by way of its carboxy-terminus, leaving the amino-terminus of the peptide available to react with a cell-targeting construct. Thus, the cell-targeting construct preferably comprises a carboxyl functional group that can react with the terminal amine of the peptide. Cell-targeting constructs that instead comprise a hydroxyl or amino functional group can be modified to comprise a carboxyl functional group, for example, by reacting the hydroxyl or amino group with succinate anhydride. In such a case, the peptide (A)/ligand (B) structure will have an intervening coupling moiety (W) (e.g., —$C(O)(CH_2)_2C(O)$—). When a maleimido-containing coupling agent is used, the cell-targeting construct preferably comprises a sulfhydryl functional group, which can form a bond with the maleimido moiety.

Other coupling moieties (W) can be used to facilitate attachment of the peptide (A) to position X of Formula I (—W-A or W-A-B), link the peptide to the cell-targeting construct (-A-W—B), or both (—W-A-W—B). For instance, a maleimido-based coupling agent can be used to attach a cysteine-containing peptide (A) to position X of Formula I, resulting in a coupling moiety (W) of the formula

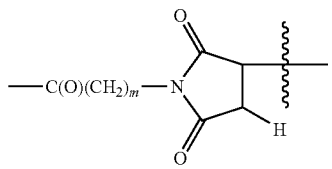

intervening between the azonafide-based ring and the peptide (A). When an N-hydroxysuccinidyl-based coupling agent is used instead, the resulting coupling moiety (W) will generally be of the formula —C(O)(CH$_2$)$_m$—. An extended polyamine coupling agent also can be used to produce a coupling moiety of the formula —(CH$_2$)$_m$NH—.

The cell-targeting construct preferably is an antibody (or similar tumor-selective protein such as an affibody), a ligand, or other peptide or peptidomimetic compound. The term "peptidomimetic" as used herein refers to a compound containing non-peptidic structural elements that is capable of mimicking or antagonizing the biological action(s) of a natural parent peptide. One example of a peptidomimetic is a peptoid. The term "peptoid" as used herein refers to a peptidomimetic that results from the oligomeric assembly of N-substituted glycines.

Desirably, the cell-targeting construct (e.g., ligand, antibody, or other molecule) specifically binds to a cell receptor of the targeted cell type (e.g., a cancer cell). The term "specifically bind" means that the cell-targeting construct binds to a particular type of cell receptor with preference, or with higher affinity, than to another type of cell receptor. Cell receptors expressed by desired target cell types (e.g., cancer cells) include, for example, the gastrin receptor, the cholecystokinin A (CCKA) receptor, the somatostatin receptor, the gastrin-releasing peptide (GRP) receptor, the substance P receptor, the guanylin receptor, and the vasoactive intestinal peptide 1 (VIP-1) receptor. Thus, the cell-targeting construct can be, for example, a ligand, antibody, or other molecule that binds to any of the foregoing receptors. Specific examples of ligands that bind these receptors include, without limitation, the ligands presented in Table 1. Other cell receptors and target proteins include Her2, CD20, EGFR, CA125, CD22, VEGF, CD52, CD33, CD3, and CD25. Thus, the cell targeting construct can be, for example, a ligand, antibody, or other molecule that binds to any such receptors or proteins (e.g., an anti-Her2, anti-CD20, anti-EGFR, anti-CA125, anti-CD22, anti-VEGF, anti-CD52, anti-CD33, anti-CD3, or anti-CD25 antibody). Specific examples of antibodies that bind to such receptors or proteins include, without limitation, trastuzumab, pertuzumab, tositumomab, cetuximab, rituximab, oregovomab, epratuzumab, bevacizumab, alemtuzumab, gemtuzumab, muromonab-CD3, ibritumomab, daclizumab.

According to another aspect of the invention, the cell-targeting construct is a peptide comprising an amino acid sequence that is cleaved by a protease secreted by, or residing on the cell surface of, the target cell (e.g., cancer cell). Desirably, the protease is secreted by, or resides on the surface of the desired target cell type (e.g., a cancer cell), but not on other cell types (e.g., a non-cancer cell). Some proteases that are overexpressed in cancer or tumor cells include glandular Kallikrein 2 (prostate-specific proteases), prostate specific antigen (psa), matrix metalloproteases (MMPs-2 and -9), urokinase plasminogen activator (uPA), and legumain. Specific examples of such peptides are listed in Table 2. The peptides are preferably attached at the C-terminus of these sequences. Without wishing to be bound by any particular theory, it is believed that compounds of Formula I comprising such peptides as cell-targeting constructs are cell-impermeable; however, upon cleavage of the peptide sequence by a protease, yield a cytotoxic compound that can enter the cell.

TABLE 1

| Ligand | SEQ ID NO | Receptor |
| --- | --- | --- |
| LGPQGPPHLVADPSKKQGPWLEEEEEAYGWMDF | 9 | Gastrin |
| W (Nle) DF | 10 | Gastrin |
| D(SfY)MGWMDF | 11 | CCKA |
| D(SfY)(Nle)GW(Nle)DF (SfY = sulfated tyrosine) | 12 | CCKA |
| VPLPAGGGTVLTKMYPRGNHWAVGHLM | 13 | GRP |
| WAVGHLM | 14 | GRP |
| AGCKNFFWKTFTSC | 15 | Somatostatin |
| FCFWKTCT(OH)† | 16 | Somatostatin |
| RPLPQQFFGLM | 17 | Substance P |
| PGTCEICAYAACTGC | 18 | Guanylin |
| NDDCELCVACTGCL | 19 | Guanylin |
| NYCCELCCNPACTGCF | 20 | Guanylin |
| HSDALFTDNYTRLRLQMAVKKYLNSILNG | 21 | VIP-1 |
| HSDALFTDNYTRLRLQ(Nle)AVKKYLNSILNG | 22 | VIP-1 |
| EEEAYGW(Nle)DF | 23 | Gastrin |

†(OH) indicates that the terminal hydroxyl group is not amidated.

TABLE 2

| Protease-Cleavable Peptide ("*" indicates cleavage point) | SEQ ID NO | Protease |
| --- | --- | --- |
| GKAFR*R*L | 24 | Kallikrein 2 |
| Mu-HSSKLQ*L (Mu = Morpholinocarbonyl) | 25 | psa |
| Ac-EPCitG*HopYL (Hop = homophenylalanine; Cit = citrulline) | 26 | MMPs-2 and -9 |
| LGGSGR*SANAILE | 27 | uPA |
| Suc-β-AN*L | 28 | legumain |

R$_1$ of Formula I is selected from the group consisting of hydrogen, alkyl, alkyloxy, alkynoyl, alkylthiol, formyl, halogen, aryl, nitro, sulfanyl, hydrazino, amino, oxyamino, alkylamino, dialkylamino, or any combination thereof. Preferably, R$_1$ is a C$_1$-C$_6$ alkoxy, more preferably C$_1$-C$_3$ alkoxy, especially ethoxy (—OCH$_2$CH$_3$) or methoxy (—OCH$_3$), SCH$_3$, or a dialkylamino alkylamino (e.g., NH(CH$_2$)$_x$—N(CH$_3$)$_2$, wherein x=2, 3, or 4).

R$_2$ is selected from the group consisting of hydrogen, alkyl, alkyloxy, alkynoyl, alkylthiol, formyl, halogen, aryl, nitro, sulfanyl, hydrazino, amino, oxyamino, alkylamino, dialkylamino, or any combination thereof, or R$_2$ is —(CH$_2$)$_2$—. Preferably, R$_2$ is a C$_1$-C$_6$ alkyl, more preferably a C$_1$-C$_3$ alkyl, especially ethyl (—CH$_2$CH$_3$) or methyl (—CH$_3$).

When R$_2$ is —(CH$_2$)$_2$—, the groups R$_2$, Z, and (CH$_2$)—, together with the nitrogens to which they are attached, form a piperazine moiety. An exemplary illustration of this configuration of Formula II is show below.

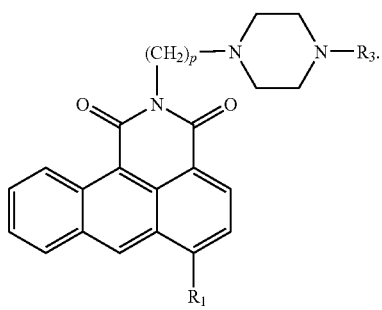

The compounds of Formula I can be prepared by any suitable method. However, the invention also provides compounds of Formula II, which are especially useful for the preparation of a compound of Formula I. The invention, thus, provides a compound of Formula II that can be used for the preparation of a compound of Formula I or for any other purpose.

According to Formula II, $R_3$ can be H, —$(CH_2)_qNH_2$, —$(CH_2)_qNH$—Y, —$(CH_2)_qNH$-A-Y, —Y, or -A-Y, wherein Y is H, —$C(O)(CH_2)_m$-T, or -A-$C(O)(CH_2)_m$-T, T is a maleimido group or an N-hydroxysuccinimide ester, and A, m, and q are as described with respect to the compound of Formula I. $R_1$, $R_2$, Z, n, and p of Formula II also are as described with respect to Formula I.

One advantage of the compound of Formula II is that it can be readily attached to a peptide linker and, optionally, to a cell-targeting construct, preferably by a single-step reaction. For instance, when Y is H, the amino group of which it is part can form a bond with the carboxy-terminus of a peptide (A) to provide a compound of Formula I, wherein X is a peptide (A). This is illustrated in general reaction scheme (i):

(i)

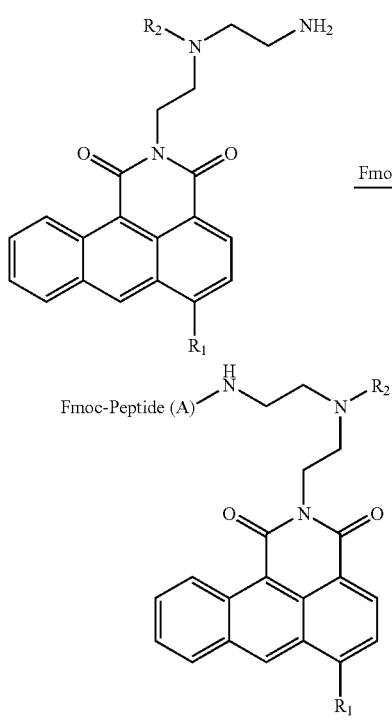

Similarly, when Y is —$C(O)(CH_2)_m$—Z or -A-$C(O)(CH_2)_m$—Z, and Z is a maleimido group, the Y group can be reacted with the sulfhydryl group of a peptide or cell-targeting construct, as appropriate, to provide a compound of Formula I. When Z is an N-hydroxysuccinimide ester, the Y group can be reacted with the primary amine of a peptide or cell-targeting construct, as appropriate, to provide a compound of Formula I. This is illustrated in general reaction schemes (ii) and (iii):

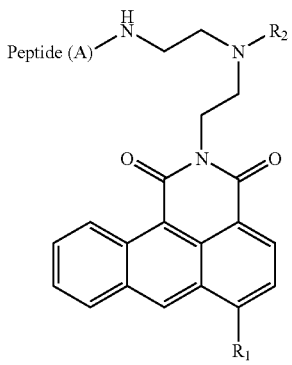

(ii)

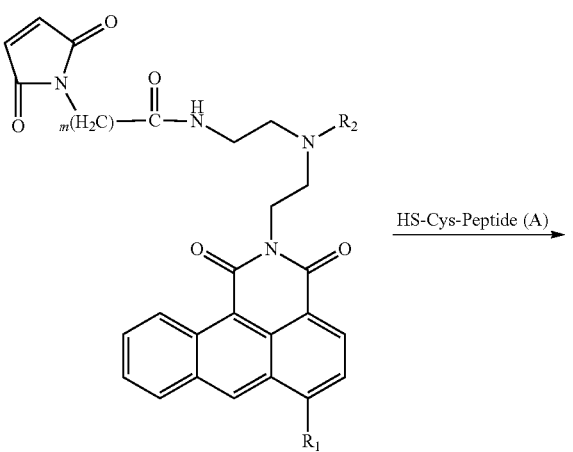

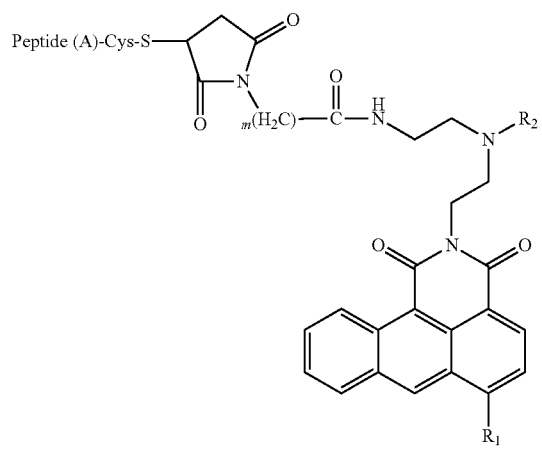

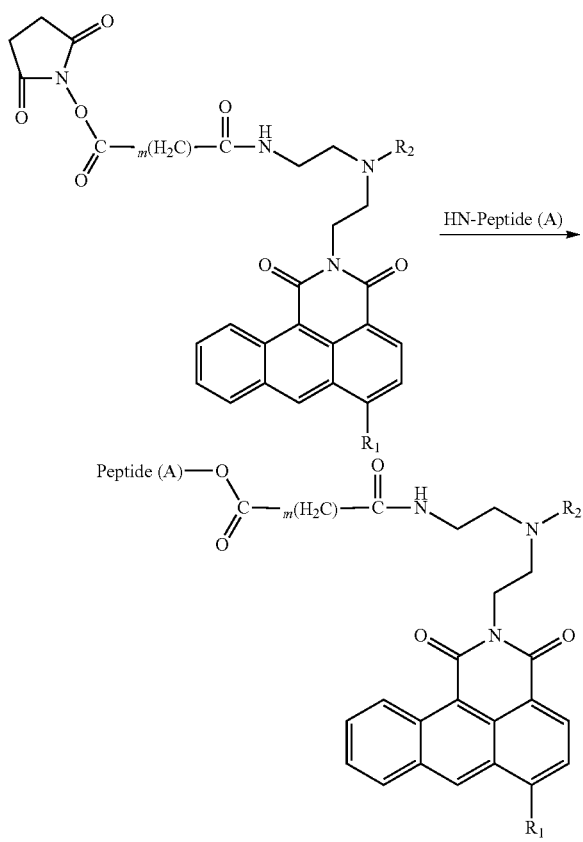

(iii)

The peptide and, when present, cell-targeting construct or coupling moiety can be added to a compound of Formula II in any order to provide a compound of Formula I. For example, the peptide can be linked to a compound of Formula II, and a cell-targeting construct subsequently linked to the peptide, or the peptide and cell-targeting construct can be joined first, and the peptide/cell-targeting construct complex subsequently linked to a compound of Formula II.

The invention, thus, provides a method of preparing a compound of Formula I comprising attaching a peptide to a compound of Formula II, whereby a compound of Formula I is prepared. The peptide can be attached to a compound of Formula II by reacting the peptide with group Y of Formula II directly, or by first reacting the Y group of Formula II or the peptide with a coupling agent. Suitable coupling agents include succinic acid anhydride, maleimido-containing coupling agents, and N-hydroxysuccinate ester-containing coupling agents. Specific examples of coupling agents include N-γ-maleimidobutyryloxy succinimide ester and octanedioic acid di-N-hydroxy succinimide ester.

The method of preparing a compound of Formula I can further comprising attaching a cell-targeting construct to the peptide, before or after attaching the peptide to the compound of Formula II. The cell-targeting construct can be attached to the peptide, for instance, by reacting the peptide with a functional group on the cell-targeting construct. When the amino-terminus of the peptide is available, for example, a carboxyl group of the cell-targeting construct can be reacted directly with the amino group of the peptide. Or, if the cell-targeting construct comprises an amine or hydroxyl functional group, the cell-targeting construct can be reacted with succinate anhydride to provide a carboxyl functional group that can react with the amino group of the peptide. Alternatively, the peptide or ligand can be reacted with a coupling agent to facilitate attaching the ligand to the peptide. For instance the peptide can be reacted with a maleimido-containing coupling agent, and the maleimido group can be attached to a sulfhydryl group of the cell-targeting construct. Or, the peptide can be reacted with a coupling agent comprising an N-hydroxysuccinimide ester, and the active ester can be used to attach the cell-targeting construct to the peptide. Protecting groups can be used during the synthesis, as appropriate. The method of preparing a compound of Formula I is further illustrated by the examples provided herein.

The present invention further provides a composition comprising a compound of Formula I or Formula II and a carrier. The carrier can be any of those conventionally used and is limited only by chemico-physical considerations, such as solubility and lack of reactivity with the compounds of the present invention, and, when applicable, by the route of administration. Preferably, the carrier is pharmaceutically acceptable especially with respect to a composition comprising a compound of Formula I. The pharmaceutically acceptable carrier should be chemically inert to the compound and should have little or no detrimental side effects or toxicity under the conditions of use. Such carriers can include a physiological saline solution; dextrose or other saccharide solution; or ethylene, propylene, polyethylene, or other glycol. Additional carriers specific to the form of the composition are discussed below.

The invention also provides a method of delivering a cytotoxic azonafide derivative to a cell comprising administering to the cell a compound of Formula I, or composition comprising same, whereupon a cytotoxic azonafide derivative is released from the compound and delivered to the cell. As previously mentioned, and without wishing to be bound by any particular theory, it is believed that the compound of Formula I, which comprises a peptide and, optionally, a cell-targeting construct at position X, is stable in the circulation; however, upon specific cellular interaction of the compound, or interaction with a protease, it is believed that the peptide is cleaved, thereby releasing a cytotoxic azonafide derivative. All aspects of the compound of Formula I used in conjunction with the method are as previously described herein.

The method can be used to deliver the cytotoxic azonafide derivative to any cell for any purpose. The cell is preferably a cancer cell, and the cell can be in vitro or in vivo. Any type of cancer can be targeted by selecting the appropriate cell-targeting construct. Examples of suitable cancer types include cancers of the skin, lung, stomach, throat, salivary glands, colon, breast, prostate, pancreas, ovaries, uterus, endometrial tubes, as well as, leukemia, melanoma, renal cell carcinoma, multiple myeloma, and any other cancer that can be inhibited (e.g., inhibition of growth or proliferation) by an azonafide based compound.

The method is especially useful to research, treat, or inhibit cancer or a tumor in a host. Thus, the invention provides, as a related aspect, a method of treating or preventing cancer or a tumor in a mammal comprising administering to the mammal an anti-cancer or anti-tumor effective amount of a compound of Formula I. An "anti-cancer" or "anti-tumor" effective amount is an amount sufficient to treat or inhibit, to any degree, the onset or progression of a cancer or tumor.

For purposes of the present invention, mammals include, but are not limited to, the order Rodentia, such as mice, and the order Logomorpha, such as rabbits, the order Carnivora, including Felines (cats) and Canines (dogs), the order Artiodactyla, including Bovines (cows) and Suines (pigs), the order Perssodactyla, including Equines (horses), the order Primate, Ceboid, or Simoid (monkeys), or the order Anthropoids (humans and apes). An especially preferred mammal is the human.

The dose administered to a mammal, particularly a human, in the context of the present invention should be sufficient to effect a therapeutic response in the mammal over a reasonable time frame. The dose will be determined by the strength of the particular compound or composition administered and the condition of the mammal (e.g., human), as well as the body weight of the mammal (e.g., human) to be treated. The size of the dose also will be determined by the existence, nature, and extent of any adverse side effects that might accompany the administration of a particular compound or composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration of the compound in pharmaceutical compositions for topical administration is 0.05 to 15% (by weight). A preferred concentration is from 0.02 to 5%. A more preferred concentration is from 0.1 to 3%. Ultimately, the attending physician will decide the dosage and the amount of the compound of the invention with which to treat each individual patient, taking into consideration a variety of factors, such as age, body weight, general health, diet, sex, compound or composition to be administered, route of administration, and severity of the disease being treated.

The compound of Formula I, or composition thereof, can be administered alone or in combination with other suitable components. Such components include, for example, compounds that aid in the delivery of a cytotoxic agent in a cell-specific manner, or that assist in treatment or inhibition of cancer or tumors, for example, other anti-cancer or anti-tumor compounds.

One skilled in the art will appreciate that suitable methods of administering the compound of the present invention or composition thereof to a mammal such as a human, are known, and, although more than one route can be used to administer a particular composition, a particular route can provide a more immediate and more effective reaction than another route.

Formulations suitable for oral administration can consist of (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Methods for the formulation and preparation of pharmaceutical compositions are well known in the art and are described in, for example, *Remington's Pharmaceutical Sciences*, Mack Publishing Company, Philadelphia, Pa., 17th ed. (1985), *The Merck Index*, 11th ed., (Merck & Co. 1989), and Langer, *Science*, 249, 1527-1533 (1990).

With respect to any of the inventive methods of treating or preventing a disease, including the inventive method of treating tumors, the composition administered can be any of the inventive compositions described herein. Thus, the method of treating or preventing a disease can further comprises any one or more steps or aspects of the method of preparing a composition, as described herein.

As used herein, the terms "treat," and "prevent" as well as words stemming therefrom, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

The following examples further illustrate the invention but, of course, should not be construed as in any way limiting its scope.

Example 1

The following example illustrates the preparation of a compound of Formula II by a multi-step process.

A. Preparation of 5-chloro-aceanthrylene-1,2-dione

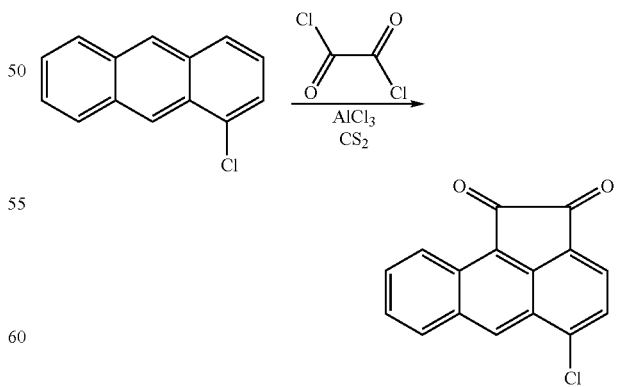

Anhydrous aluminum chloride (3.5 g, 26.2 mmol) was added to a cold (0° C.) mixture of 1-chloroanthracene (3 g, 14.1 mmol) and oxalyl chloride (10 g, 78.8 mmol) in 30 ml of dry carbon disulfide. After stirring the reaction mixture under an argon atmosphere for two hours at 0° C., additional portions of anhydrous carbon disulfide (30 ml) and dry aluminum chloride (2.25 g, 18.7 mmol) were added. Stirring at 0° C. was continued for an additional two hours. Thereafter, an additional portion of anhydrous carbon disulfide (10 ml) was added, and stirring was continued overnight at room temperature. At the end of the reaction, the mixture was cooled to 0° C. and dilute hydrochloric acid was slowly added. An orange precipitate was collected, washed with water, and treated with 5% sodium hydroxide solution (150 ml). The insoluble solid was collected, washed with water, and air-dried. The crude material was purified by short-column filtration using silica gel and chloroform. Yield was 53%.

B. Preparation of
4-chloro-anthracene-1,9-dicarboxylic acid

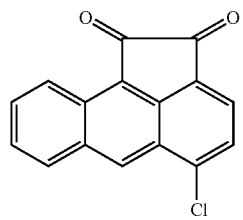

$\xrightarrow[\text{1,2-dioxan}]{\text{H}_2\text{O}_2 \atop \text{2M NaOH}}$

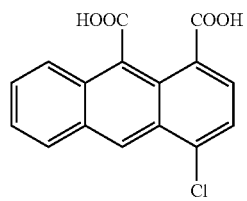

5-chloro-aceanthrylene-1,2-dione (1.49 g, 5.59 mmol) was suspended in a mixture of 10 ml of 2 M sodium hydroxide and 50 ml of 1,4-dioxan. The mixture was cooled to 15° C. and treated with 8.5 ml of 30% hydrogen peroxide. After 10 minutes at 15° C., stirring was continued at room temperature for additional 45 minutes. The reaction mixture was diluted with 100 ml of water and an orange insoluble precipitate was collected by filtration. The filtrate was acidified using dilute sulfuric acid, and a yellow precipitate was collected, washed with water, and dried overnight under vacuum. The yield was 96%.

C. Preparation of
6-chloro-2-oxa-benzo[de]anthracene-1,3-dione

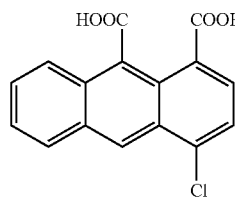

$\xrightarrow[\text{reflux}]{\text{Ac}_2\text{O}}$ 4-chloro-anthracene-1,9-dicarboxylic acid (1.6 g, 5.35 mmol) was placed in a 50 ml flask and mixed with 25 ml of acetic anhydride. The mixture was refluxed under argon at 170° C. for six hours and left at room temperature overnight to crystallize. An orange precipitate was collected by filtration, washed five times with dry diethyl ether (15 ml), and dried under vacuum overnight. The yield was 93%.

D. Preparation of 6-chloro-2-(2-methylaminoethyl)-1,2-dihydro-3H-dibenzo[de,h]isoquinoline-1,3-dione

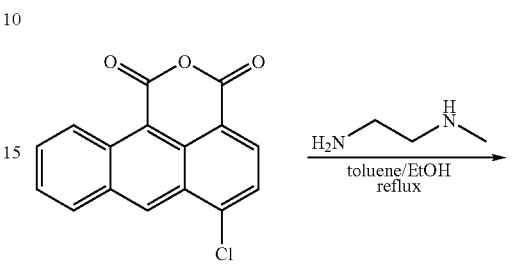

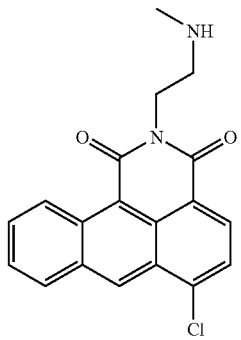

Method A: 6-chloro-2-oxa-benzo[de]anthracene-1,3-dione (1 g, 3.54 mmol) was suspended in the mixture of anhydrous toluene (60 ml), anhydrous ethanol (10 ml), and AP-methyl-ethane-1,2-diamine (350 μl, 3.77 mmol). The mixture was heated under reflux conditions (120° C.) for twelve hours. After cooling to room temperature, the solvent was evaporated and a crude material was collected. The crude material was purified by low-pressure column chromatography using basic alumina and chloroform with gradient of methanol. The yield was 88%.

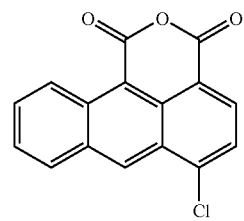

$\xrightarrow[\text{reflux}]{\text{toluene/EtOH}}$

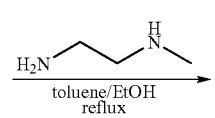

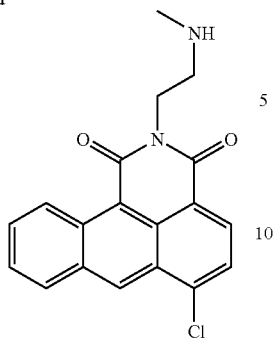

Method B: In alternative method B, the synthesis used dicarboxylic acid (4-chloro-anthracene-1,9-dicarboxylic acid) instead of corresponding anhydride (6-chloro-2-oxa-benzo[de]anthracene-1,3-dione). All other conditions remain unchanged.

E. Preparation of 6-methoxy-2-(2-methylaminoethyl)-1,2-dihydro-3H-bibenzo[de,h]isoquinoline-1,3-dione

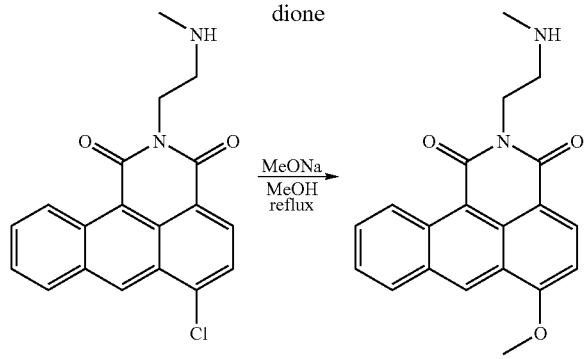

150 ml of anhydrous methanol sodium methoxide (0.56 g, 10.4 mmol) was added to the 6-chloro-2-(2-methylaminoethyl)-1,2-dihydro-3H-dibenzo[de,h]isoquinoline-1,3-dione (1.058 g, 3.12 mmol). The reaction mixture was refluxed under argon at 100° C. for 10 hours and, after cooling to room temperature, the solvent was evaporated and a crude material was collected. The crude material was purified by low-pressure column chromatography using a silica column (40 g) and chloroform with a gradient of methanol. The yield was 76%.

F. Preparation of 2-{[2-(6-Methoxy-1,3-dioxo-1H,3H-dibenzo[de,h]isoquinolin-2-yl)-ethyl]-methyl-amino}-ethyl)-carbamic acid tert-butyl ester

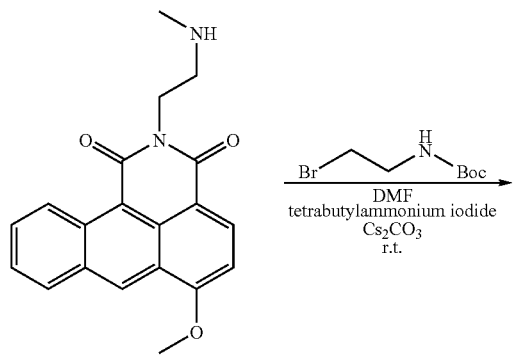

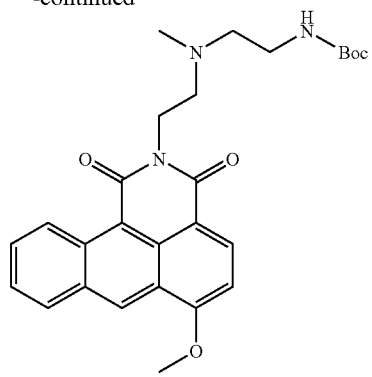

Cesium carbonate (777 mg, 4.76 mmol) was added to a solution of 797 mg of 6-methoxy-2-(2-methylaminoethyl)-1,2-dihydro-3H-bibenzo[de,h]isoquinoline-1,3-dione (2.38 mmol) in dry DMF tert-butyl N-(2-bromoethyl)carbamate (534 mg, 4.76 mmol). The reaction mixture was stirred over argon at room temperature for eight days. An additional portion of tent-butyl N-(2-bromoethyl)carbamate (534 mg, 4.76 mmol) was added after the first two days of the reaction. The reaction was monitored by HPLC-ESI-MS technique. After completion, the reaction mixture was evaporated using a vacuum, and a crude product was collected. The crude product was purified by low-pressure column chromatography using a silica gel column and chloroform with a gradient of methanol. The yield was 58%.

G. Preparation of 2-{2-[(2-aminoethyl)methylamino]ethyl}-6-methoxy-1,2-dihydro-3H-dibenzo[de,h]isoquinoline-1,3-dione (MDD117)

Method (i)—Removing Boc protection by Preparing Hydrochloride Salt: The hydrochloric salt of 2-{2-[(2-aminoethyl)methylamino]ethyl}-6-methoxy-1,2-dihydro-3H-dibenzo[de,h]isoquinoline-1,3-dione was prepared by stirring (2-{[2-(6-Methoxy-1,3-dioxo-1H,3H-dibenzo[de,h]isoquinolin-2-yl)-ethyl]-methyl-amino}-ethyl)-carbamic acid tert-butyl ester with 4M HCl in dry dioxane for 40 minutes. The reaction was quantitative.

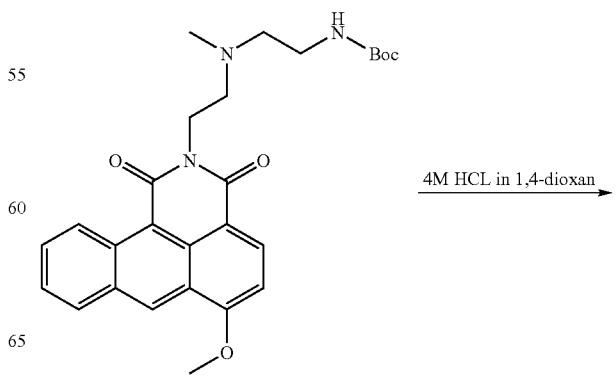

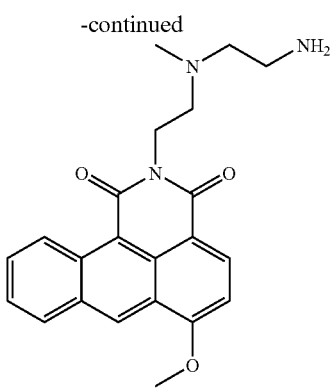

x 2 HCl

Method (ii)—Removing Boc protection by Preparing Trifluoroacetic salt: The trifluoroacetic salt of 2-{2-[(2-aminoethyl)methylamino]ethyl}-6-methoxy-1,2-dihydro-3H-dibenzo[de,h]isoquinoline-1,3-dione was prepared by stirring (2-{[2-(6-Methoxy-1,3-dioxo-1H,3H-dibenzo[de,h]isoquinolin-2-yl)-ethyl]-methyl-amino}-ethyl)-carbamic acid tert-butyl ester with 50% trifluoroacetic acid in DCM for 40 minutes. The reaction was quantitative.

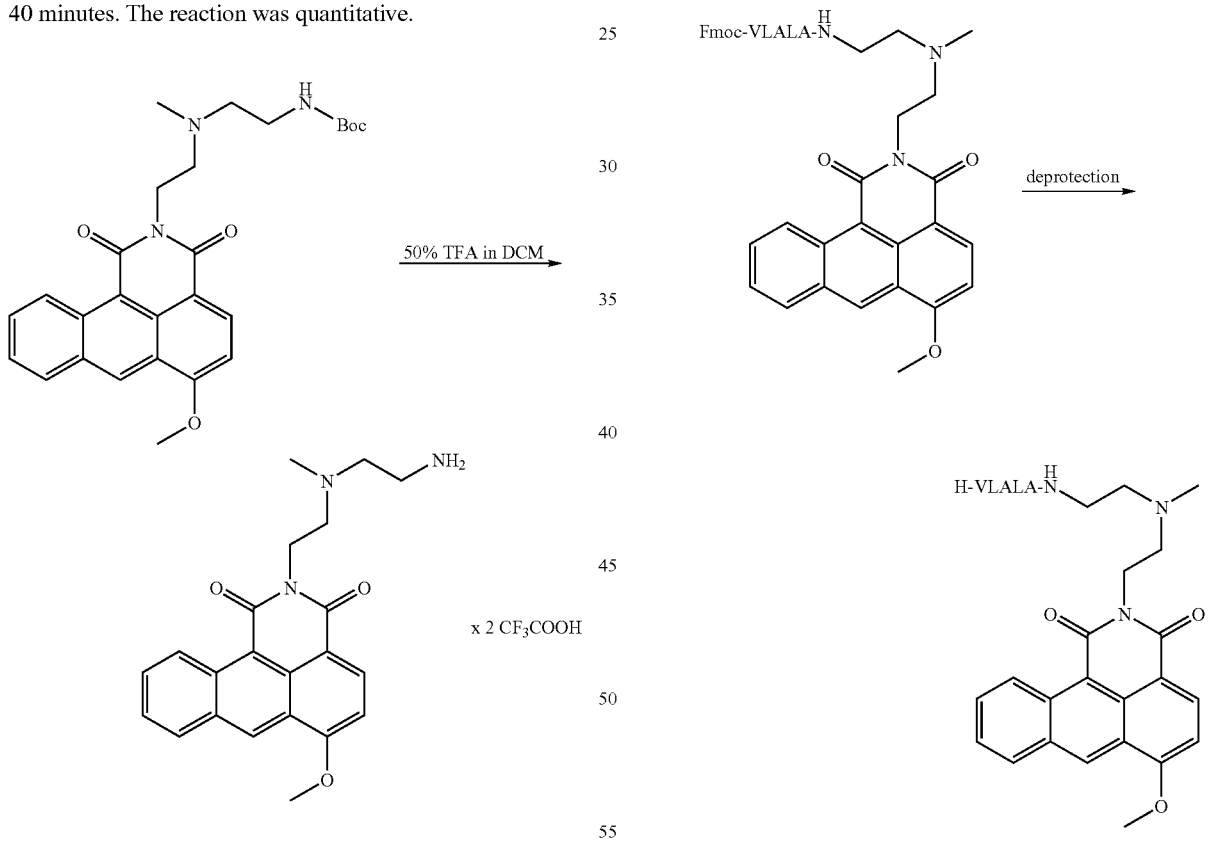

50% TFA in DCM x 2 CF₃COOH

After removing Boc protection by method (i) or method (ii), a compound of Formula II was recovered.

Example 2

This example illustrates the preparation of a compound of Formula I by attaching a peptide and a ligand to a compound of Formula II.

A peptide with the sequence VLALA was prepared with an Fmoc protecting group at the amino-terminus (e.g., Fmoc-VLALA-OH). The peptide was prepared on a commercially available ABI433 peptide synthesizer using standard Fmoc peptide chemistry and a preloaded Wang-type resin. The peptide was cleaved from resin without removing N-terminal Fmoc protection using mixture of 95% TFA, 2.5% of TIS and 2.5% of water. After HPLC purification on C18 reverse phase column, peptide was used directly for the next reaction.

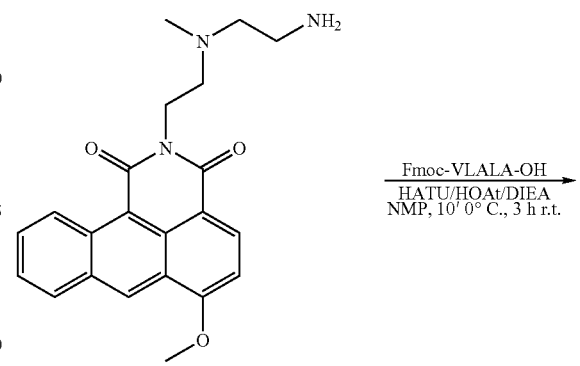

Fmoc-VLALA-OH
HATU/HOAt/DIEA
NMP, 10' 0° C., 3 h r.t.

deprotection 0.1 mmol of the Fmoc-VLALA-OH peptide and 0.07 mmol of MD117 (Example 1, Step G) were dissolved in 5 ml of anhydrous NMP. The mixture was cooled to 0° C. and stirred under argon. Thereafter, 0.1 mmol of HOAt and 0.1 mmol of HATU (2-(1H-7-Azabenzotriazol-1-yl)-1,1,3,3-tetramethyl uronium hexafluorophosphate methanaminium) were added to the cold mixture, followed by the addition of 0.5 mmol of DIEA. The reaction was kept at 0° C. for 10 minutes, and then kept at room temperature for three hours. The reaction mixture was evaporated and a crude product was collected. The crude product was purified by low-pressure column chromatography using a silica gel column and chloroform with gradient of methanol. The purified Fmoc-protected intermediate was dissolved in 5 ml of 25% piperidine in DMF and stirred for 40 minutes to deprotect the compound. After evaporation, the material was purified by preparative HPLC using C18 column. The deprotected compound is referred to as MD125.

A gastrin ligand having the sequence Glu-Glu-Ala-Tyr-Gly-Trp-Nle-Asp-Phe was synthesized on ABI433 peptide synthesizer (0.1 mmol scale) using an amide resin and standard Fmoc peptide chemistry. After the last deprotection step, peptide on the resin was reacted for 40 min with succinic anhydride (100 equivalents) in the presence of DIEA and catalytic amount of HOBt to faun the sequence Suc-Glu-Glu-Ala-Tyr-Gly-Trp-Nle-Asp-Phe, wherein Suc corresponds to the succinyl group.

The resin was washed several times with NMP, and MD125 (0.0325 mmol) was added followed by the addition of HATU (0.1 mmol), HOAt (0.1 mmol), and DIEA (0.3 mmol). The resin was stirred by argon bubbling for four hours. Then the resin was drained, washed five times with NMP, five times with DCM, and five times with methanol. After drying in vacuum, the compound was cleaved from the resin with a mixture of 95% TFA, 2.5% TIS and 2.5% water over 2 h. After filtration and evaporation, the final compound was purified by preparative HPLC using an Agilent Zorbax 300SB-C3 column (21.2×250 mm, 7μ, 300 Å). The final compound of Formula I is referred to as MD133.

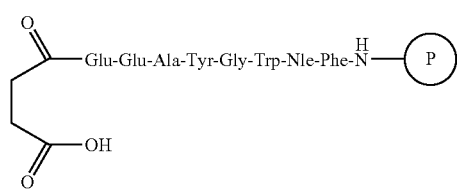
+

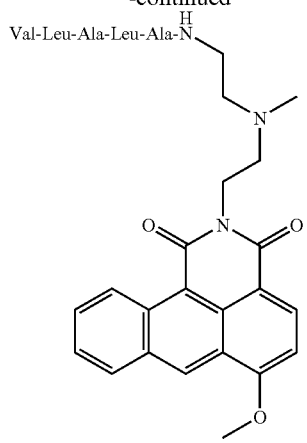

1. HATU/HOAt/DIEA
2. TFA:TIS:water 95:2.5:2.5

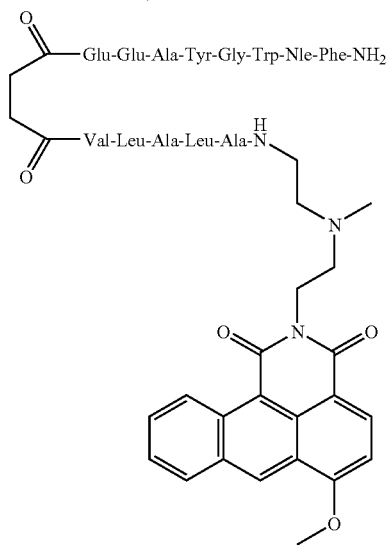

Example 3

This example illustrates the preparation of a compound of Formula II comprising an activated N-hydroxysuccinimide ester.

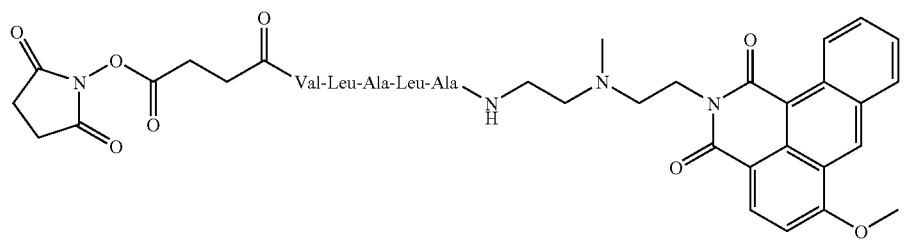

A. Synthesis of Fmoc-VLALA-OH peptide

A Fmoc-VLALA-OH peptide was prepared on an ABI433 peptide synthesizer (Applied Biosystems) using standard Fmoc peptide chemistry and a preloaded Wang-type resin. The peptide was cleaved from the resin without removing N-terminal Fmoc protection using a mixture of 95% TFA, 2.5% TIS and 2.5% water. After HPLC purification on C18 reverse phase column, peptide was used directly for the next reaction.

B. Synthesis of Fmoc-VLALA-MD117 conjugate (MD160)

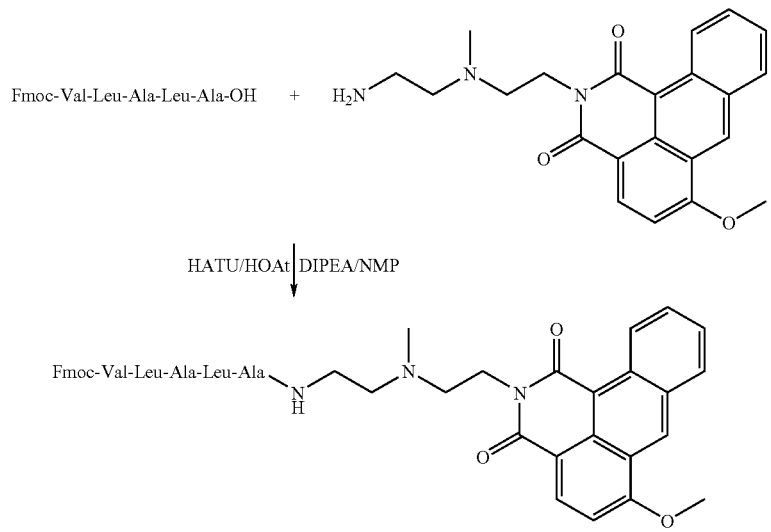

The conjugate (MD160) was prepared in anhydrous NMP by coupling Fmoc-VLALA-OH (0.25 mmol) with 0.25 mmol MD117 (Example 1, Step G) using HATU/HOAt/DIEA activation. When the reaction was completed the reaction mixture was evaporated and the crude product was used directly for the next reaction without purification.

C. Synthesis of Suc-VLALA-MD-117 conjugate (MD 161)

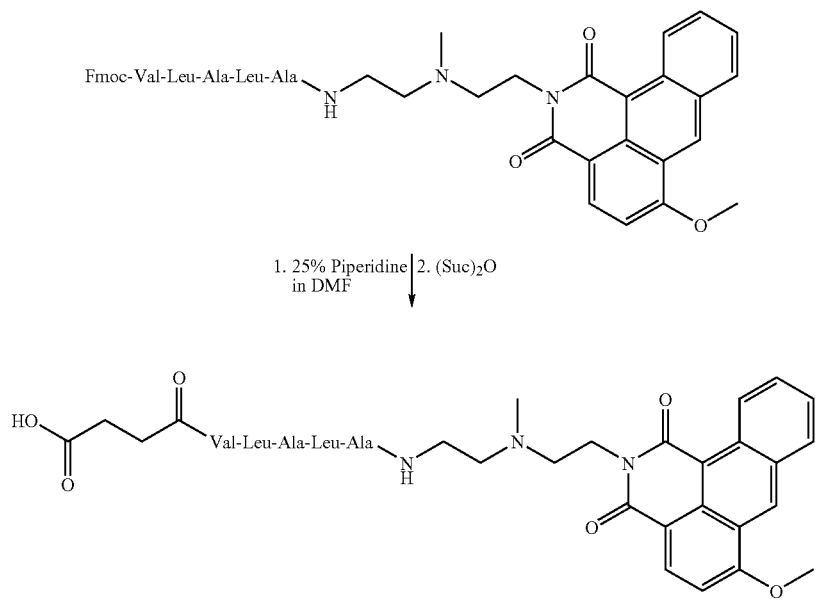

The crude MD160 was deprotected by 25% piperidine in DMF over 40 minutes. After deprotection, the solvent was evaporated and crude material was left over high vacuum for 2 h. Crude material was dissolved in dry DMF and reacted with 10 equivalents (2.5 mmol) of succinic anhydride ("(Suc)₂ O") in the presence of 20 equivalents of DIEA and catalytic amount of HOBt (1.1 eq). After 1 h, reaction mixture was evaporated to dryness and purified by HPLC purification on C18 reverse phase column.

D. Synthesis of HOSu-Suc-MD117 (MD165)

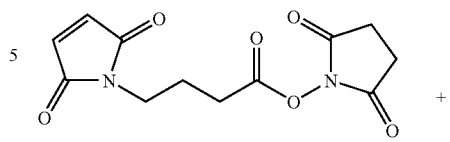

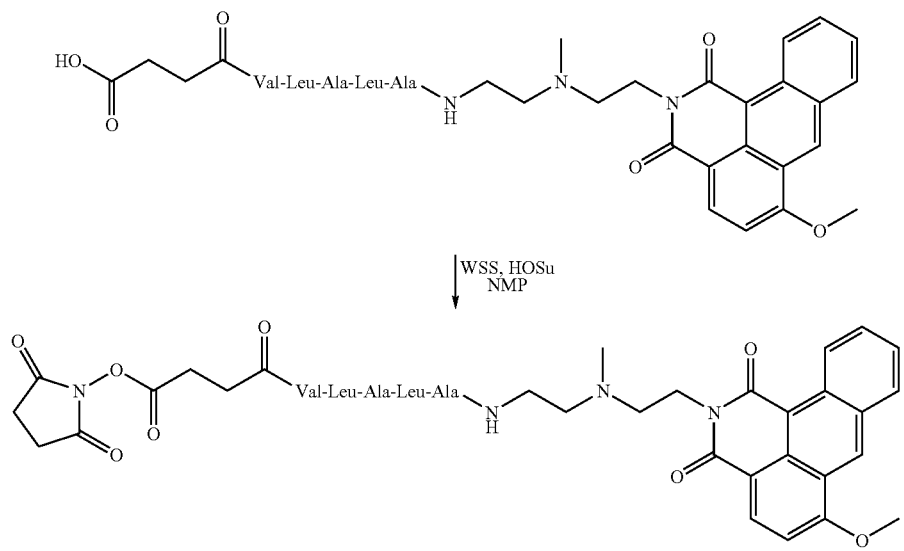

Suc-MD125 (MD161) was mixed with 1.2 equivalents of N-hydroxysuccinimide (HOSu) and 1.1 equivalents of EDAC hydrochloride (WSC×HCl; 1-Ethyl 3-(3-Dimethyl Amino Propyl) Carbodiimide) in anhydrous NMP. The reaction mixture was stirred under argon overnight, evaporated on vacuum rotary evaporator and purified using HPLC and C18 reverse phase column. A compound of Formula II comprising an activated N-hydroxysuccinimide ester was recovered as HOSu-Suc-MD117 (MD165).

Example 4

The following example illustrates the preparation of a compound of Formula II comprising an a maleimido group (4-(2, 5-Dioxo-2,5-dihydro-pyrrol-1-yl)—N-(2-{[2-(6-methoxy-1,3-dioxo-1H,3H-dibenzo[de,h]isoquinolin-2-yl)-ethyl]-methyl-amino}-ethyl)-butyramide)) (MD166).

0.138 mmol of 2-{2-[(2-aminoethyl)methylamino]ethyl}-6-methoxy-1,2-dihydro-3H-dibenzo[de,h]isoquinoline-1,3-dione (MD117; Example 1, Step G)×2 TFA (trifluoroacetic acid) was dissolved in 2 ml of anhydrous DMF, and 50 mg (0.178 mmol) of GMBS (N-γ-maleimidobutyryloxy succinimide ester) was added followed by the addition of 80 μl (0.450 mmol) of DIEA. The reaction mixture was stirred at room temperature under argon for four hours. After completion of the reaction, the solvent was evaporated and a crude product was collected. The crude product was purified by HPLC using a reverse phase C18 column and a water/acetonitrile solvent system with 0.1% of TFA as ion pairing reagent. The total yield of MD166 was 30%.

-continued

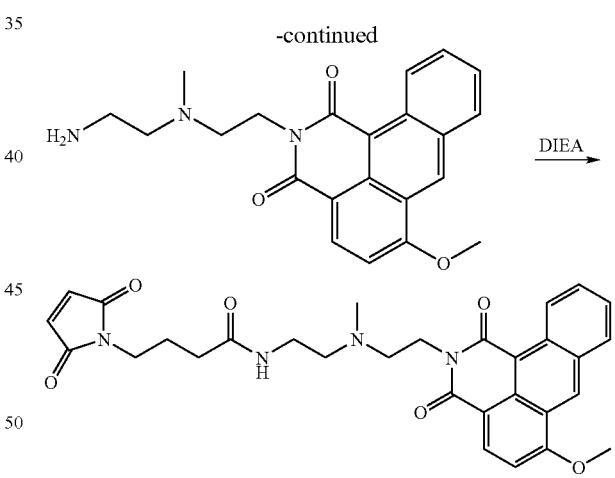

Example 5

The following example illustrates the preparation of a compound of Formula II comprising an activated N-hydroxysuccinimide ester (7-(2-{[2-(6-Methoxy-1,3-dioxo-1H,3H-dibenzo[de,h]isoquinolin-2-yl)-ethyl]-methyl-amino}-ethylcarbamoyl )-heptanoic acid 2,5-dioxo-pyrrolidin-1-yl ester) (MD167).

0.130 mmol of 2-{2-[(2-aminoethyl)methylamino]ethyl}-6-methoxy-1,2-dihydro-3H-dibenzo[de,h]isoquinoline-1,3-dione (MD117; Example 1, Step G)×2HCl in anhydrous DMF (1 ml) was added by slowly dropping over 30 minutes to a stirred mixture of 0.260 mmol (95.6 mg) DSS (octanedioic acid di-N-hydroxysuccinimide ester; PIERCE biotechnology) and 0.389 mmol (69 μl) DIEA in 5 ml of anhydrous DMF. The reaction mixture was stirred for an additional two and one-half hours, then solvent was evaporated. The formation of the dimer (MD168) as a major byproduct was observed. The crude product was purified by HPLC using a reverse phase C18 column and a water/acetonitrile solvent system with 0.1% of TFA as ion pairing reagent. Total MD167×TFA yield after purification was 56%.

pared compound of Formula I contained about 2.1 mol of MD167 azonafide derivative per trastuzumab antibody molecule.

The conjugate was tested on a lung cancer cell line (Calu-3) overexpressing Her2/neu using MTT cell toxicity assay. As Table 3 below shows, the compound of Formula I showed much higher growth inhibition activity when compared to the trastuzumab antibody itself.

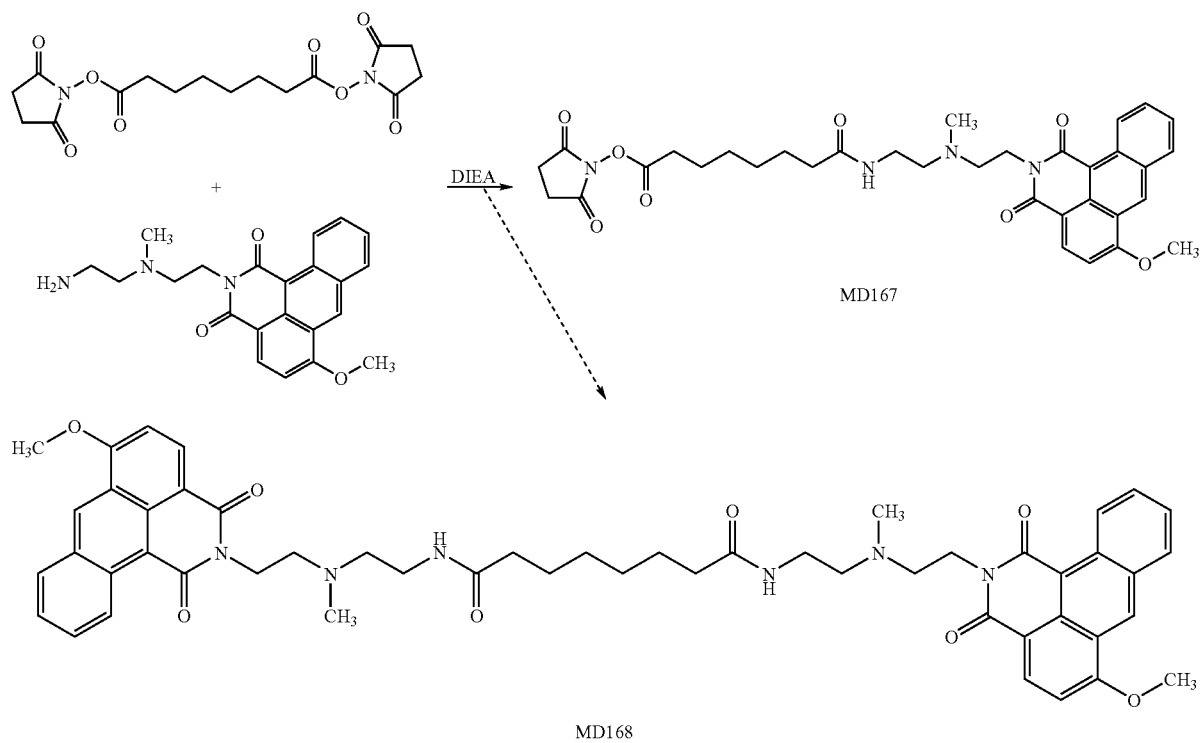

Example 6

This example illustrates the synthesis and testing of a compound of Formula I, wherein B is an antibody against Her2/Nue.

60 mg of a trastuzumab preparation containing 30 mg of antibody was dissolved in 1.5 ml water. The solution was dialyzed against phosphate buffered saline ("PBS") at pH 7.2 for 24 hours with three changes of buffer in a Pierce Biotech. Inc. dialysis unit. A 10K cut-off was used.

1.37 mg (1.84 mmol) of MD167 (Example 5) (MW=744) was dissolved in 70 μl of acetonitrile (26 nmol/uL). Then, 3.8 mg (53 nmol) of trastuzumab in 0.4 ml PBS were mixed with 40 μl (1040 nmol) of MD 167 solution. The resulting mixture was incubated in a cold room overnight and subjected to gel-filtration on a Pharmacia desalting 5 ml column equilibrated with PBS.

UV spectra were used for calculation of the degree of substitution assuming that 0.2 mM of a reference MD117 (Compound of Formula II; Example 1, Step G) has an absorbance (A)=2.7 at 468 nm and 7.59 at 278 nm, and that 20 mg/ml trastuzumab has an A=26.3 at 278 nm and MW=150000. The substitution analysis showed that the pre-

TABLE 3

| Concentration (nM) | Cell Number, % From Control | |
|---|---|---|
| | Trastuzumab | Compound of Formula I |
| 1 | 64 | 70 |
| 10 | 62 | 67 |
| 50 | 47 | 36 |
| 100 | 54 | 1.8 |

Example 7

This example illustrates the administration of a compound of Formula I to a cell.

Gastrin receptor-expressing rat pancreatic cells (NIH line AR42J) were exposed in vitro to four different concentrations (10 nM, 50 nM, 100 nM, and 1000 nM) of MD 133 (Compound of Formula I, Example 2) or MD 117 (Compound of Formula II; Example 1, Step G) for a period of about five days. The number of viable cells left in the culture after the five day period was measured, and compared to a control culture that was not exposed either compound. The number of cells remaining in each of the experimental cultures, expressed as a percentage of viable cells in the control culture, is provided in Table 4, below. Table 4 also provides the IC50 (concentration of a drug that is required for 50% inhibition) and LC50 (the median concentration required for death of 50% of the cell population) calculated from the data.

As the table below shows, MD117, a cytotoxic compound of Formula II, exhibited a very low LC50, killing all cells in the culture at each of the tested concentrations. An IC50 could not be calculated from this data. By way of contrast, MD133, which is a compound of Formula I prepared by adding a peptide and ligand to MD117, yielded an IC50 of about 50 nM and an LC 50 of about 800 nM. These results demonstrate the compound of Formula II exhibited significantly reduced overall toxicity, while retaining a desirable receptor-mediated cytotoxic response.

TABLE 4

|                    | % Viable Cells |         |
|--------------------|----------------|---------|
| Concentration (nM) | MD117          | MD133   |
| 10                 | −100           | 73      |
| 50                 | −100           | 53      |
| 100                | −100           | 27      |
| 1000               | −100           | −79     |
| LC50               | 3 nM           | 800 nM  |
| IC50               | N/A            | 50 nM   |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of Formula I:

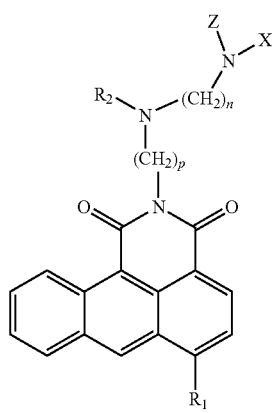

Formula I wherein n is 1-8;
p is 2-4;
X is —(CH$_2$)$_q$NH-A, —(CH$_2$)$_q$NH-A-B, —(CH$_2$)$_q$NH-A-W—B, -A, -A-B, -A-W—B, -W-A, —W-A-B, or —W-A-W—B, wherein A is a peptide comprising two or more amino acids, B is a cell-targeting construct, W is a coupling moiety selected from the group consisting of —(CH$_2$)$_m$NH—, —C(O)(CH$_2$)$_m$C(O)—, —C(O)(CH$_2$)$_m$—, and

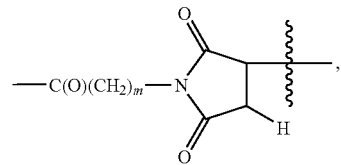

m is 1-16 and q is 1-8;
Z is hydrogen, methyl, or, when n is 2 and R$_2$ is —(CH$_2$)$_2$—, Z is a bond between R$_2$ and the nitrogen to which Z is attached;
R$_1$ is selected from the group consisting of hydrogen, alkyl, alkoxy, alkynoyl, alkylthiol, formyl, halogen, aryl, nitro, sulfanyl, hydrazino, amino, oxyamino, alkylamino, dialkylamino, and combinations thereof; and
R$_2$ is selected from the group consisting of hydrogen, alkyl, alkoxy, alkynoyl, alkylthiol, formyl, halogen, aryl, nitro, sulfanyl, hydrazino, amino, oxyamino, alkylamino, dialkylamino, and combinations thereof, or R$_2$ is —(CH$_2$)$_2$—.

2. The compound of claim 1, wherein A is a peptide selected from the group consisting of VLALA (SEQ ID NO: 1), FALA (SEQ ID NO: 2), ALAL (SEQ ID NO: 3), ALALA (SEQ ID NO: 4), ChaLALA (SEQ ID NO: 5), ChaChaLAL (SEQ ID NO: 6), NalChaLAL (SEQ ID NO: 7), and NalLALA (SEQ ID NO: 8).

3. The compound of claim 2, wherein A is VLALA (SEQ ID NO: 1).

4. The compound of claim 1, wherein W is —C(O)(CH$_2$)$_m$C(O)—.

5. The compound of claim 1, wherein m is 2.

6. The compound of claim 1, wherein B is an antibody, a peptide or a peptidomimetic compound.

7. The compound of claim 6, wherein B is selected from the group consisting of EEEAYGW(Nle)DF (SEQ ID NO: 23), W(Nle)DF (SEQ ID NO: 10), and LGPQGPPHL-VADPSKKQGPWLEEEEEAYGWMDF (SEQ ID NO: 9).

8. The compound of claim 6, wherein B is an anti-Her2, anti-CD20, anti-EGFR, anti-CA125, anti-CD22, anti-VEGF, anti-CD52, anti-CD33, anti-CD3, or anti-CD25 antibody.

9. The compound of claim 6, wherein B is an antibody against Her2/Nue.

10. The compound of claim 6, wherein B is selected from the group consisting of GKAFRRL (SEQ ID NO: 24), Mu-HSSKLQL (SEQ ID NO: 25), Ac-EPCitGHopYL (SEQ ID NO: 26), LGGSGRSANAILE (SEQ ID NO: 27), and Suc-β-ANL (SEQ ID: NO 28).

11. The compound of claim 1, wherein X is A-B or A-W—B.

12. A compound of Formula II:

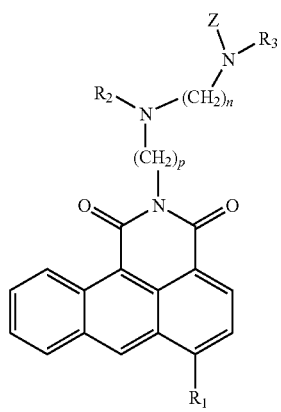

Formula II wherein n is 1-8;
p is 2-4;
R$_3$ is H, —(CH$_2$)$_q$NH—Y, —(CH$_2$)$_q$NH-A-Y, —Y, or -A-Y, wherein A is a peptide comprising two or more amino acids, Y is a coupling moiety selected from the group consisting of

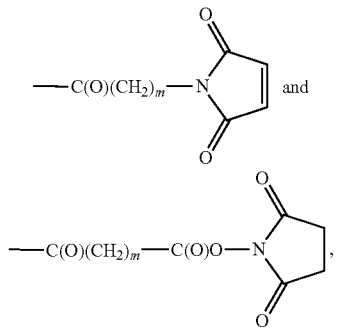

and m is 1-16 and q is 1-8;

Z is hydrogen or methyl;

R₁ is selected from the group consisting of hydrogen, alkyl, alkoxy, alkynoyl, alkylthiol, formyl, halogen, aryl, nitro, sulfanyl, hydrazino, amino, oxyamino, alkylamino, dialkylamino, and combinations thereof; and R₂ is selected from the group consisting of hydrogen, alkyl, alkoxy, alkynoyl, alkylthiol, formyl, halogen, aryl, nitro, sulfanyl, hydrazino, amino, oxyamino, alkylamino, dialkylamino, and combinations thereof.

13. The compound of claim 12, wherein A is a peptide selected from the group consisting of VLALA (SEQ ID NO: 1), FALA (SEQ ID NO: 2), ALAL (SEQ ID NO: 3), ALALA (SEQ ID NO: 4), ChaLALA (SEQ ID NO: 5), ChaChaLAL (SEQ ID NO: 6), NalChaLAL (SEQ ID NO: 7), and NalLALA (SEQ ID NO: 8).

14. The compound of claim 13, wherein A is VLALA (SEQ ID NO: 1).

15. The compound of claim 12, wherein $R_3$ is H.

16. The compound of claim 12, wherein n is 2.

17. The compound of claim 12, wherein $R_1$ is a $C_1$-$C_6$ alkoxy.

18. The compound of claim 17, wherein $R_1$ is methoxy.

19. The compound of claim 12, wherein $R_2$ is a $C_1$-$C_6$ alkyl.

20. The compound of claim 19, wherein $R_2$ is methyl.

21. The compound of claim 1, wherein the compound is

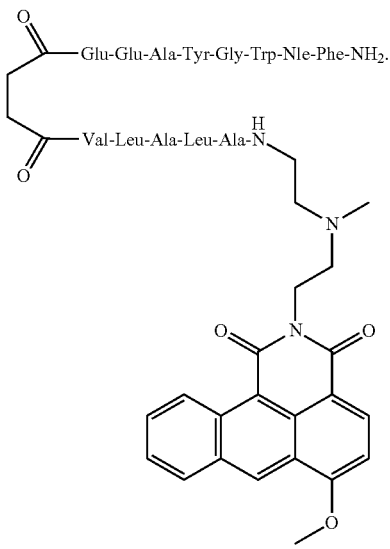

22. The compound of claim 12, wherein the compound is

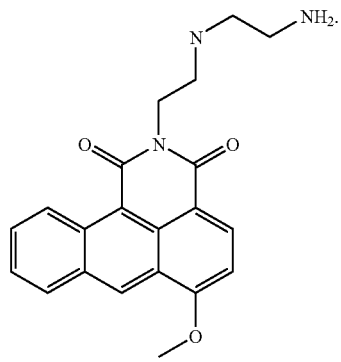

23. The compound of claim 12, wherein the compound is

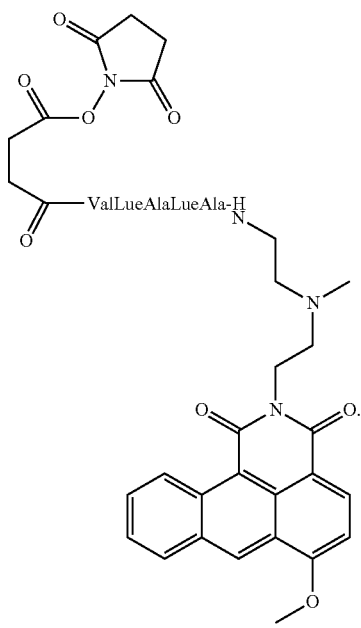

24. The compound of claim 12, wherein the compound is

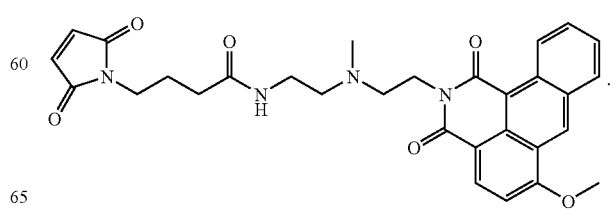

25. The compound of claim 12, wherein the compound is

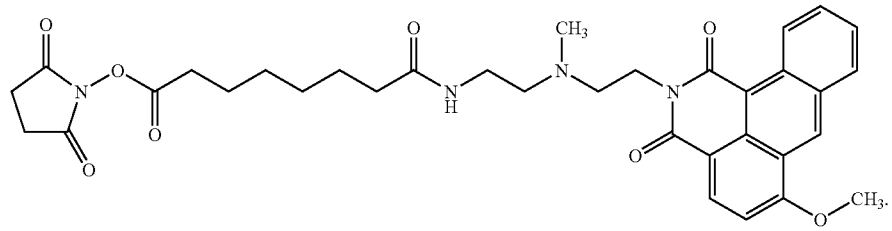

26. A composition comprising the compound of claim 1 and a carrier.

27. A method of delivering a cytotoxic azonafide derivative to a cell comprising administering to the cell a compound of claim 1, whereupon a cytotoxic azonafide derivative is released from the compound and delivered to the cell.

28. The method of claim 27 wherein the cell is a cancer or tumor cell.

29. The method of claim 28, wherein the cell is in vivo.

30. A method of preparing a compound of Formula I:

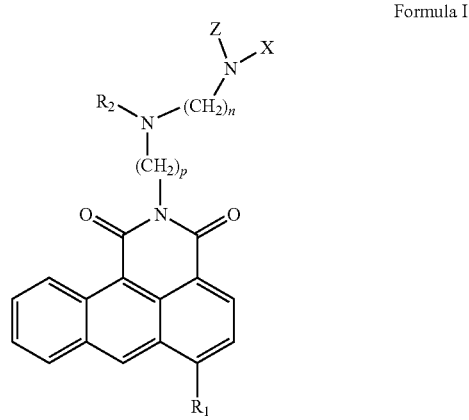

Formula I wherein n is 1-8;
p is 2-4;
X is —$(CH_2)_q$NH-A, —$(CH_2)_q$NH-A-B, —$(CH_2)_q$NH-A-W—B, -A, -A-B, -A-W—B, —W-A, —W-A-B, or —W-A-W—B, wherein A is a peptide comprising two or more amino acids, B is a cell-targeting construct, W is a coupling moiety selected from the group consisting of —$(CH_2)_m$NH—, —$C(O)(CH_2)_mC(O)$—, —$C(O)(CH_2)_m$—, and

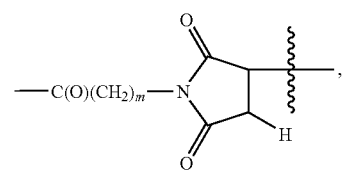

m is 1-16 and q is 1-8;
Z is hydrogen, methyl, or, when n is 2 and $R_2$ is —$(CH_2)_2$—, Z is a bond between $R_2$ and the nitrogen to which Z is attached;
$R_1$ is selected from the group consisting of hydrogen, alkyl, alkoxy, alkynoyl, alkylthiol, formyl, halogen, aryl, nitro, sulfanyl, hydrazino, amino, oxyamino, alkylamino, dialkylamino, and combinations thereof;
$R_2$ is selected from the group consisting of hydrogen, alkyl, alkoxy, alkynoyl, alkylthiol, formyl, halogen, aryl, nitro, sulfanyl, hydrazino, amino, oxyamino, alkylamino, dialkylamino, and combinations thereof, or $R_2$ is —$(CH_2)_2$—;
said method comprising attaching a peptide or peptidomimetic to $R_3$ of a compound of claim 12, whereby a compound of Formula I is prepared.

31. The method of claim 30 further comprising attaching a cell-targeting construct to the peptide or peptidomimetic.

32. The method of claim 31, wherein the peptide is selected from the group consisting of VLALA (SEQ ID NO: 1), FALA (SEQ ID NO: 2), ALAL (SEQ ID NO: 3), ALALA (SEQ ID NO: 4), ChaLALA (SEQ ID NO: 5), ChaChaLAL (SEQ ID NO: 6), NalChaLAL (SEQ ID NO: 7), and NalLALA (SEQ ID NO: 8).

33. The method of claim 31, wherein the cell-targeting construct is a ligand selected from the group consisting of EEEAYGW(Nle)DF (SEQ ID NO: 23), W(Nle)DF (SEQ ID NO: 10), and LGPQGPPHLVADPSKKQGPWLEEEEE-AYGWMDF (SEQ ID NO: 9).

34. The method of claim 31, wherein the cell-targeting construct is an anti-Her2, anti-CD20, anti-EGFR, anti-CA125, anti-CD22, anti-VEGF, anti-CD52, anti-CD33, anti-CD3, or anti-CD25 antibody.

35. The method of claim 31, wherein the cell-targeting construct is an antibody against Her2/Nue.

36. The method of claim 31, wherein the cell-targeting construct is a peptide selected from the group consisting of GKAFRRL (SEQ ID NO: 24), Mu-HSSKLQL (SEQ ID NO: 25), Ac-EPCitGHopYL (SEQ ID NO: 26), LGGSGRSAN-AILE (SEQ ID NO: 27), and Suc-β-ANL (SEQ ID: NO 28).

37. A compound of Formula II:

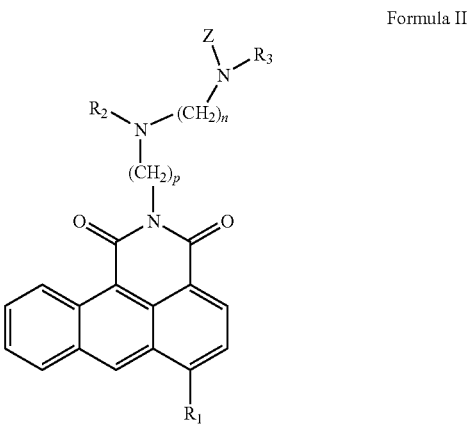

Formula II wherein n is 1-8;
p is 2-4;
$R_3$ is —$(CH_2)_q NH_2$ and q is 1-8;
Z is hydrogen, methyl, or, when n is 2 and $R_2$ is —$(CH_2)_2$—, Z is a bond between $R_2$ and the nitrogen to which Z is attached;
$R_1$ is selected from the group consisting of hydrogen, alkyl, alkoxy, alkynoyl, alkylthiol, formyl, halogen, aryl, nitro, sulfanyl, hydrazino, amino, oxyamino, alkylamino, dialkylamino, and combinations thereof; and
$R_2$ is selected from the group consisting of alkyl, alkoxy, alkynoyl, alkylthiol, formyl, halogen, aryl, nitro, sulfanyl, hydrazino, amino, oxyamino, alkylamino, dialkylamino, and combinations thereof, or $R_2$ is —$(CH_2)_2$—.

38. A compound of Formula II:

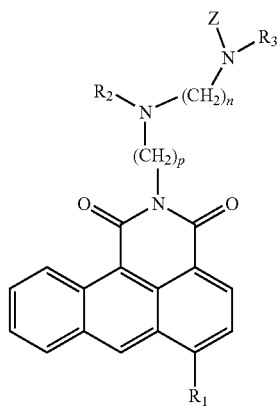

Formula II wherein n is 1-8;
p is 2-4;
$R_3$ is —$(CH_2)_q NH_2$, —$(CH_2)_q NH$—Y, —$(CH_2)_q NH$-A-Y, -Y, or -A-Y, wherein A is a peptide comprising two or more amino acids, Y is a coupling moiety selected from the group consisting of

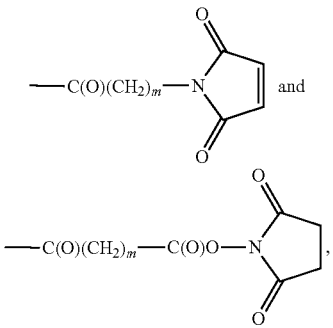

m is 1-16 and q is 1-8;
Z is a bond between $R_2$ and the nitrogen to which Z is attached;
$R_1$ is selected from the group consisting of hydrogen, alkyl, alkoxy, alkynoyl, alkylthiol, formyl, halogen, aryl, nitro, sulfanyl, hydrazino, amino, oxyamino, alkylamino, dialkylamino, and combinations thereof; and
$R_2$ is —$(CH_2)_2$—.

39. The compound of claim 38, wherein the compound is

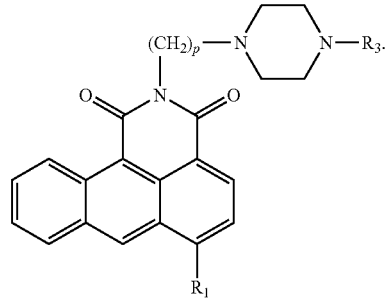

* * * * *

SEQUENCE LISTING

<160> NUMBER OF SEQ ID NOS: 28

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Val Leu Ala Leu Ala
1               5

<210> SEQ ID NO 2
<211> LENGTH: 4
<212> TYPE: PRT
<213> ORGANISM: Artificial
<220> FEATURE:
<223> OTHER INFORMATION: Synthetic

<400> SEQUENCE: 2

Phe Ala Leu Ala
1

<210> SEQ ID NO 3
<211> LENGTH: 4
<212> TYPE: PRT
<213> ORGANISM: Artificial

-continued

```
<220> FEATURE:
<223> OTHER INFORMATION: Synthetic

<400> SEQUENCE: 3

Ala Leu Ala Leu
1

<210> SEQ ID NO 4
<211> LENGTH: 5
<212> TYPE: PRT
<213> ORGANISM: Artificial
<220> FEATURE:
<223> OTHER INFORMATION: Synthetic

<400> SEQUENCE: 4

Ala Leu Ala Leu Ala
1               5

<210> SEQ ID NO 5
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: "Xaa" is 2-cyclohexyl-L-alanine (Cha).

<400> SEQUENCE: 5

Xaa Leu Ala Leu Ala
1               5

<210> SEQ ID NO 6
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: "Xaa" is 2-cyclohexyl-L-alanine (Cha).

<400> SEQUENCE: 6

Xaa Xaa Leu Ala Leu
1               5

<210> SEQ ID NO 7
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: "Xaa" is 1-naphthyl-alanine (Nal).
<220> FEATURE:
<221> NAME/KEY: misc_feature
<222> LOCATION: (2)..(2)
<223> OTHER INFORMATION: "Xaa" is 2-cyclohexyl-L-alanine (Cha).

<400> SEQUENCE: 7

Xaa Xaa Leu Ala Leu
1               5

<210> SEQ ID NO 8
<211> LENGTH: 5
<212> TYPE: PRT
```

```
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: "Xaa" is 1-naphthyl-alanine (Nal).

<400> SEQUENCE: 8

Xaa Leu Ala Leu Ala
1               5

<210> SEQ ID NO 9
<211> LENGTH: 33
<212> TYPE: PRT
<213> ORGANISM: Artificial
<220> FEATURE:
<223> OTHER INFORMATION: Synthetic

<400> SEQUENCE: 9

Leu Gly Pro Gln Gly Pro Pro His Leu Val Ala Asp Pro Ser Lys Lys
1               5                   10                  15

Gln Gly Pro Trp Leu Glu Glu Glu Glu Ala Tyr Gly Trp Met Asp
            20                  25                  30

Phe

<210> SEQ ID NO 10
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: "Xaa" is norlucine (Nle).

<400> SEQUENCE: 10

Trp Xaa Asp Phe
1

<210> SEQ ID NO 11
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: "Xaa" is a sulfated tyrosine (SfY).

<400> SEQUENCE: 11

Asp Xaa Met Gly Trp Met Asp Phe
1               5

<210> SEQ ID NO 12
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: "Xaa" is a sulfated tyrosine (SfY).
<220> FEATURE:
<221> NAME/KEY: misc_feature
<222> LOCATION: (3)..(3)
<223> OTHER INFORMATION: "Xaa" is norlucine (Nle).
```

```
<220> FEATURE:
<221> NAME/KEY: misc_feature
<222> LOCATION: (6)..(6)
<223> OTHER INFORMATION: "Xaa" is norlucine (Nle).

<400> SEQUENCE: 12

Asp Xaa Xaa Gly Trp Xaa Asp Phe
1               5

<210> SEQ ID NO 13
<211> LENGTH: 27
<212> TYPE: PRT
<213> ORGANISM: Artificial
<220> FEATURE:
<223> OTHER INFORMATION: Synthetic

<400> SEQUENCE: 13

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25

<210> SEQ ID NO 14
<211> LENGTH: 7
<212> TYPE: PRT
<213> ORGANISM: Artificial
<220> FEATURE:
<223> OTHER INFORMATION: Synthetic

<400> SEQUENCE: 14

Trp Ala Val Gly His Leu Met
1               5

<210> SEQ ID NO 15
<211> LENGTH: 14
<212> TYPE: PRT
<213> ORGANISM: Artificial
<220> FEATURE:
<223> OTHER INFORMATION: Synthetic

<400> SEQUENCE: 15

Ala Gly Cys Lys Asn Phe Phe Trp Lys Thr Phe Thr Ser Cys
1               5                   10

<210> SEQ ID NO 16
<211> LENGTH: 8
<212> TYPE: PRT
<213> ORGANISM: Artificial
<220> FEATURE:
<223> OTHER INFORMATION: Synthetic

<400> SEQUENCE: 16

Phe Cys Phe Trp Lys Thr Cys Thr
1               5

<210> SEQ ID NO 17
<211> LENGTH: 11
<212> TYPE: PRT
<213> ORGANISM: Artificial
<220> FEATURE:
<223> OTHER INFORMATION: Synthetic

<400> SEQUENCE: 17

Arg Pro Leu Pro Gln Gln Phe Phe Gly Leu Met
1               5                   10

<210> SEQ ID NO 18
```

```
<211> LENGTH: 15
<212> TYPE: PRT
<213> ORGANISM: Artificial
<220> FEATURE:
<223> OTHER INFORMATION: Synthetic

<400> SEQUENCE: 18

Pro Gly Thr Cys Glu Ile Cys Ala Tyr Ala Ala Cys Thr Gly Cys
1               5                   10                  15

<210> SEQ ID NO 19
<211> LENGTH: 14
<212> TYPE: PRT
<213> ORGANISM: Artificial
<220> FEATURE:
<223> OTHER INFORMATION: Synthetic

<400> SEQUENCE: 19

Asn Asp Asp Cys Glu Leu Cys Val Ala Cys Thr Gly Cys Leu
1               5                   10

<210> SEQ ID NO 20
<211> LENGTH: 16
<212> TYPE: PRT
<213> ORGANISM: Artificial
<220> FEATURE:
<223> OTHER INFORMATION: Synthetic

<400> SEQUENCE: 20

Asn Tyr Cys Cys Glu Leu Cys Cys Asn Pro Ala Cys Thr Gly Cys Phe
1               5                   10                  15

<210> SEQ ID NO 21
<211> LENGTH: 29
<212> TYPE: PRT
<213> ORGANISM: Artificial
<220> FEATURE:
<223> OTHER INFORMATION: Synthetic

<400> SEQUENCE: 21

His Ser Asp Ala Leu Phe Thr Asp Asn Tyr Thr Arg Leu Arg Leu Gln
1               5                   10                  15

Met Ala Val Lys Lys Tyr Leu Asn Ser Ile Leu Asn Gly
            20                  25

<210> SEQ ID NO 22
<211> LENGTH: 29
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (17)..(17)
<223> OTHER INFORMATION: "Xaa" is norlucine (Nle).

<400> SEQUENCE: 22

His Ser Asp Ala Leu Phe Thr Asp Asn Tyr Thr Arg Leu Arg Leu Gln
1               5                   10                  15

Xaa Ala Val Lys Lys Tyr Leu Asn Ser Ile Leu Asn Gly
            20                  25

<210> SEQ ID NO 23
<211> LENGTH: 10
<212> TYPE: PRT
<213> ORGANISM: Artificial
<220> FEATURE:
<223> OTHER INFORMATION: Synthetic
```

```
<220> FEATURE:
<221> NAME/KEY: misc_feature
<222> LOCATION: (8)..(8)
<223> OTHER INFORMATION: "Xaa" is norlucine (Nle).

<400> SEQUENCE: 23

Glu Glu Glu Ala Tyr Gly Trp Xaa Asp Phe
1               5                   10

<210> SEQ ID NO 24
<211> LENGTH: 7
<212> TYPE: PRT
<213> ORGANISM: Artificial
<220> FEATURE:
<223> OTHER INFORMATION: Synthetic

<400> SEQUENCE: 24

Gly Lys Ala Phe Arg Arg Leu
1               5

<210> SEQ ID NO 25
<211> LENGTH: 7
<212> TYPE: PRT
<213> ORGANISM: Artificial
<220> FEATURE:
<223> OTHER INFORMATION: Synthetic

<400> SEQUENCE: 25

His Ser Ser Lys Leu Gln Leu
1               5

<210> SEQ ID NO 26
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: "Xaa" is citrulline (Cit).
<220> FEATURE:
<221> NAME/KEY: misc_feature
<222> LOCATION: (5)..(5)
<223> OTHER INFORMATION: "Xaa" is homophenylalanine (Hop).

<400> SEQUENCE: 26

Glu Pro Xaa Gly Xaa Tyr Leu
1               5

<210> SEQ ID NO 27
<211> LENGTH: 13
<212> TYPE: PRT
<213> ORGANISM: Artificial
<220> FEATURE:
<223> OTHER INFORMATION: Synthetic

<400> SEQUENCE: 27

Leu Gly Gly Ser Gly Arg Ser Ala Asn Ala Ile Leu Glu
1               5                   10

<210> SEQ ID NO 28
<211> LENGTH: 3
<212> TYPE: PRT
<213> ORGANISM: Artificial
```

```
<220> FEATURE:
<223> OTHER INFORMATION: Synthetic

<400> SEQUENCE: 28

Ala Asn Leu
1
```